United States Patent [19]

Gosteli et al.

[11] Patent Number: 5,292,918

[45] Date of Patent: Mar. 8, 1994

[54] DIASTEREOSELECTIVE PROCESS FOR PREPARING N-SUBSTITUTED AMINO ACIDS AND DERIVATIVES

[75] Inventors: Jacques Gosteli, Basel; Ingrid Mergelsberg, Dagmersellen; Markus Tanner, Schachen, all of Switzerland

[73] Assignee: Schering Corporation, Kenilworth, N.J.

[21] Appl. No.: 934,537

[22] PCT Filed: Mar. 29, 1991

[86] PCT No.: PCT/US91/02034

§ 371 Date: Oct. 6, 1992

§ 102(e) Date: Oct. 6, 1992

[87] PCT Pub. No.: WO91/17141

PCT Pub. Date: Nov. 14, 1991

Related U.S. Application Data

[63] Continuation-in-part of Ser. No. 514,798, Apr. 26, 1990, abandoned.

[51] Int. Cl.$^5$ .......................................... C07C 253/30
[52] U.S. Cl. .................................... 558/352; 558/348; 558/350; 558/351; 558/390; 558/441
[58] Field of Search ............... 558/332, 346, 350, 351, 558/352

[56] References Cited

U.S. PATENT DOCUMENTS 4,551,537 11/1985 Mai et al. .......................... 546/330
4,652,668 3/1987 Kim ................................... 558/390

FOREIGN PATENT DOCUMENTS 0336368 10/1989 European Pat. Off. .
3624376 1/1988 Fed. Rep. of Germany .
62-20486 8/1987 Japan .

OTHER PUBLICATIONS

P. K. Subramanian and R. W. Woodward, Synth. Commun. 16(3), pp. 337-342 (1986).
K. Weinges, G. Graab, D. Nagel and B. Stemmle, Chem. Ber. vol. 104 pp. 3594-3606 (1971).
K. Weinges, K. Gries, B. Stemmle, W. Schrank, Chem., Ber. vol. 110 pp. 2098-2105 (1977).
K. Weinges and B. Stemmle, Chem. Ber. vol. 106, pp. 2291-2297 (1973).
K. Kawashiro, S. Morimoto and H. Yoshida, Bull. Chem., Soc. Jpn, 58(7), pp. 1903-1912 (1985).
C.A. 111: 114878h, Inoue, et al., (1989), vol. 111.

*Primary Examiner*—Joseph P. Brust
*Attorney, Agent, or Firm*—Joseph T. Majka; Edward H. Mazer; James M. Gould

[57] ABSTRACT

A process for preparing an (S,S) or (R,R) diastereoisomer of the formula:

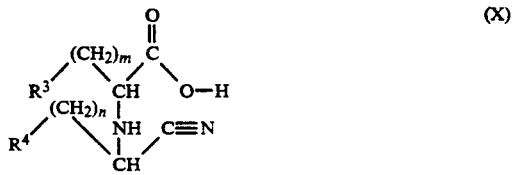

(X)

or salts, esters or amides thereof, wherein $R^3$ and $R^4$ independently represent hydrogen, alkyl, aryl or aryl substituted with halogen, alkyl, nitro or alkoxy, and n and m independently represent integers from one to six, comprising combining a cyanide compound of the formula:

$$M^1C\equiv N \qquad (III)$$

wherein $M^1$ is hydrogen, trimethylsilyl or a metal, with an optional proton source, a solvent and a Lewis acid of the formula:

$$M^2X_4, AlCl_3 \text{ or } BF_3 \qquad (IV)$$

wherein $M^2$ is Sn or Ti and X represents chloro, bromo, fluoro or iodo, with an α-amino acid compound or salts or esters thereof, followed by addition of an acyl or acetal compound to give the diastereoisomer of formula (X).

16 Claims, No Drawings

DIASTEREOSELECTIVE PROCESS FOR PREPARING N-SUBSTITUTED AMINO ACIDS AND DERIVATIVES

The present application is the U.S. national application corresponding to International Application No. PCT/US91/02034, filed Mar. 29, 1991 and designating the United States, which PCT application is in turn a continuation-in-part of U.S. application Ser. No. 07/514,798, filed Apr. 26, 1990, now abandoned, the benefit of which applications is claimed pursuant to the provisions of 35 U.S.C. §§120, 363 and 365(C).

BACKGROUND

Diastereoisomeric amino acids and derivatives are useful intermediates for preparing various pharmaceutical compounds such as enkephalinase inhibitors which are useful for treating pain or as inhibitors of the angiotensin converting enzyme (ACE) which are useful for treating hypertension or reducing elevated intraocular pressure associated with glaucoma. U.S. Pat. No. 4,652,668 discloses a process for preparing a class of pharmaceuticals useful in inhibiting angiotensin converting enzyme in humans such as N-(1-(S)-ethoxycarbonyl-3-phenylpropyl)-L-proline maleate salt is representative. German Offenlegungsschrift DE 3624376 A1 discloses a process for preparing 0-Acyl-glycosyl amines derivatives useful for preparing amino acids and derivatives by first treating an aldehyde compound with 0-acyl glycosyl amine under acidic conditions, followed by treatment with trimethylsilyl or sodium cyanide and tin or zinc (tetra)-chloride in tetrahydrofuran, isopropanol or chloroform. P. K. Subramanian and R. W. Woodward, Synth. Commun. 16 (3), pp. 337–342 (1986) disclose a four-step asymmetric Strecker synthesis for preparing (R)-(+)-2-methyl-3-phenylalanine by utilizing (S) phenylalanine as the chiral auxiliary reagent. K. Weinges, G. Graab, D. Nagel and B. Stemmle, Chem. Ber. Vol. 104, pp. 3594–3606 (1971) disclose an external asymmetric Strecker synthesis of α-methyl-amino acids. K. Weinges, K. Gries, B. Stemmle, W. Schrank, Chem. Ber. Vol. 110, pp. 2098–2105 (1977) disclose an asymmetric Strecker synthesis with (S)-(−)-1-phenylethylamine as a chiral handle to afford stereochemically homogeneous α-methyl-α-aminonitriles. K. Weinges and B. Stemmle, Chem. Ber. Vol. 106, pp. 2291–2297 (1973) disclose an asymmetric Strecker synthesis of aliphatic α-methyl-α-amino acids. S. Inoue et al. J. Chem. Soc. Chem. Comm. 1981, pp. 229. Japan Kokai Tokkyo Koho, JP 01047754 A2 Feb. 22, 1989 Heisei, JP 87-204860 Aug. 18, 1987, CA111(13):114878h discloses a process for preparing γ-1-carboxyethylamino-γ-phenylbutyronitrile and γ-phenylbutyric acid derivatives as intermediates for anti-hypertensive compounds. The article of K. Kawashiro, S. Morimoto and H. Yoshida, Gas chromatography-mass spectrometry of trimethylsilylated imino derivatives of alanine, Bull. Chem. Soc. Jpn., 58(7), pp. 1903–12 discloses trimethylsilylation of seven imino derivatives of alanine with N,O-bis(trimethylsilyl)trifluoracetamide in acetonitrile. It would be desirable to provide a process for preparing either (S,S) or (R,R) diastereoisomers in high optical yields which is relatively inexpensive and which does not require a protecting group for the amine starting material.

SUMMARY OF THE INVENTION

The present invention is directed to a process for preparing an (S,S) or (R,R) diastereoisomer of the formula:

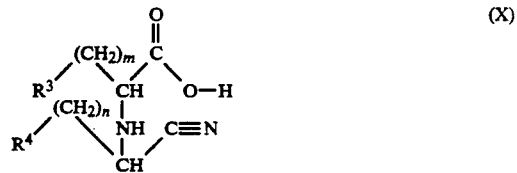

or salts, esters or amides thereof, wherein $R^3$ and $R^4$ independently represent hydrogen, alkyl, aryl or aryl substituted with halogen, alkyl, nitro or alkoxy, and n and m independently represent integers from one to six, comprising combining a cyanide compound of the formula:

$$M^1C\equiv N \quad (III)$$

wherein $M^1$ is hydrogen, trimethylsilyl or a metal, with an optionally added proton source, a solvent and a Lewis acid of the formula:

$$M^2X_4, AlCl_3 \text{ or } BF_3 \quad (IV)$$

wherein $M^2$ is Sn or Ti and X represents chloro, bromo, fluoro or iodo, with an optically active α-amino acid compound of formula (I):

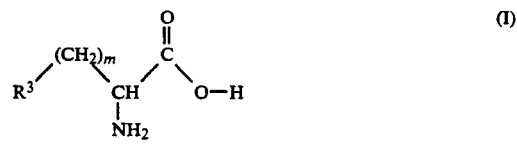

or salts, esters or amides thereof, wherein $R^3$ and m are as defined hereinbefore, followed by addition of an acyl or acetal compound of the formula (II):

or

wherein m, n and $R^4$ are as defined hereinbefore, $R^1$ is hydrogen, alkyl or phenyl and $R^2$ and $R^3$ independently represent alkyl or cycloalkyl, to give the diastereoisomer of formula (X).

The present invention has the advantage of preparing diastereoisomers of formula (X). That is, either the (S,S) or the (R,R) diastereoisomer can be prepared by selection of the desired optically active α-amino acid (I) beforehand. The present process advantageously uses as few or fewer steps than other processes previously taught. The present process has the further advantage of utilizing relatively inexpensive starting materials or reagents that are commonly available compared with other known processes, thereby reducing the overall cost of the process. Another advantage is that the present process can employ unprotected primary α-amino acids, and thus eliminates the additional costs and steps associated with such use of protecting groups as described in DE 3624376, supra. The present process also provides higher yields because more starting material is converted to the desired diastereoisomer rather than forming a racemic mixture.

DETAILED DESCRIPTION OF THE INVENTION

The term "diastereoisomer" generally refers to any group of four optical isomers occurring in compounds containing two asymmetric carbon atoms or two optically active centers, as defined in Gessner G. Hawley(ed.), The Condensed Chemical Dictionary, 10th Edition, Van Nostrand Reinhold Company Inc., New York, 1981, 1135 pp., whose teachings are incorporated herein by reference.

The stereospecificity of the diastereoisomer (X) can be determined beforehand by the appropriate selection of the α-amino acid compound (I), the nature of the metal cyanide and the Lewis Acid. For example, if one uses the α-amino acid compound (I) which is predominantly the optically active S enantiomer, the present process will yield the diastereoisomer (X) which possesses predominantly the (S,S) diastereoisomer. Similarly, if one uses the α-amino acid compound (I) which is predominantly the optically active R enantiomer, the present process will yield the (R,R) diastereoisomer. The stereochemistry of the diastereoisomer compounds (X) is referenced with regard to the two optically active centers for this compound:

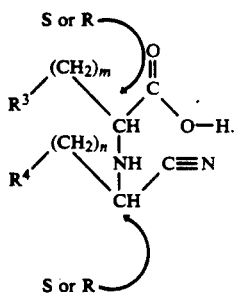

(X)

The term "alkyl" (including the alkyl portions of alkoxy)—represents a straight or branched, saturated hydrocarbon chain preferably having from 1 to 6 carbon atoms, such as methyl, ethyl, isopropyl, n-propyl, n-butyl, t-butyl, pentyl, hexyl and the like.

The term "aryl" represents a carbocyclic group having from 6 to 14 carbon atoms and having at least one fused benzenoid ring, with all available substitutable carbon atoms of the carbocyclic group being intended as possible points of attachment. Preferred aryl groups are phenyl, 1-naphthyl, 2-naphthyl and indanyl. The term "substituted aryl" refers to said carbocyclic group being optionally substituted with 1 to 3 moieties independently selected from halo, alkyl, alkoxy or nitro. Representative substituted aryl groups include methylphenyl, chlorophenyl, 1-methylnapthyl and the like.

Cyanide compounds of the formula $M^1C\equiv N$ (III) wherein $M^1$ is hydrogen, trimethylsilyl or a metal which can be sodium, potassium, lithium, cesium, iron, nickel, cadmium and zinc are well-known compounds. Suitable cyanide reagents include hydrogen cyanide (HCN), trimethylsilyl cyanide ($CNSi(CH_3)_3$), iron dicyanide ($Fe(CN)_2$), cadmium dicyanide ($Cd(CN)_2$), zinc dicyanide ($Zn(CN)_2$), sodium cyanide (NaCN), lithium cyanide (LiCN), cesium cyanide (CsCN) and potassium cyanide (KCN), preferably sodium cyanide and potassium cyanide.

The Lewis acid compounds of formula (IV) are well-known compounds as defined in J. March, Advanced Organic Chemistry, Reactions, Mechanisms, and Structure, 3rd Edition, John Wiley & Sons. New York, (1985) 1346 pages. Such Lewis Acids include aluminium trichloride ($Al(Cl_3)$) and boron trifluoride ($BF_3$). Preferably, M is Sn and X in the formula $M^2X_4$ is chloro, otherwise known as tin tetrachloride.

The acyl or acetal compounds of formula (II) are known, such as described in Houben Weyl, Methoden der Organischen Chemie, Band 7, Georg Thieme Verlag Stuttgart, 1954. Also preferred is that $R^1$ of acyl compound (IIa) is hydrogen. The most preferred compound of formula (IIa) is phenylacetaldehyde. Alternatively, $R^1$ can be alkyl or phenyl. An acetal of formula (IIb) can also be employed in place of acyl (IIa), wherein $R^1$, $R^2$, $R^3$, $R^4$ and n are as defined hereinbefore. Mixtures of acyl (IIa) and acetal (IIb) can also be employed.

The α-amino acid compounds (I) are also well known, as described in E. P. Greenstein, Chemistry of the Amino Acids, RE Krieger Publishing Co., Malabar, Fla. 1984, Vol. 1-3.

The salt forms of diastereoisomer (X) or α-amino acid (I) can be prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia or sodium bicarbonate. Examples of suitable acids for such salt formation are hydrochloric, sulfuric, phosphoric, acetic, citric, oxalic, malonic, salicylic, malic, fumaric and other mineral and carboxylic acids known to those skilled in the art.

The esters or amides of diastereoisomer (X) or α-amino acid (I) can be prepared by conventional procedures such as described in J. March, supra or in Tetrahedron Letters Vol. 36, pp. 2409 (1980).

The acyl or acetal compounds of formula (II) can be contacted with the α-amino acid compound of formula (I) in amounts effective to give the desired diastereoisomers of formula (X). Such amounts can range from excess to about 0.5:1 (moles acyl compound (II): mole of α-amino acid compound (I)), more preferably from about 5 moles to about equimolar amounts of acyl compound (II), most preferably from about 1.7 to about equimolar amounts of acyl compound (II).

The cyanide compound of formula (III) can be contacted with the α-amino acid compound of formula (I) in amounts ranging from excess to about 0.1 moles cyanide compound (III): mole of compound (I), more preferably from about 10 moles to about equimolar amounts of cyanide compound (III), most preferably about equimolar amounts of cyanide compound (III).

The Lewis Acid of formula (IV) can be contacted with the α-amino acid compound of formula (I) in amounts ranging from a molar excess to about equimolar amounts of the Lewis Acid compound (IV): mole α-amino acid compound (I). More preferably, from about 10 moles to about equimolar amounts of halogenated compound (IV), are reacted. Most preferably from about 3 to about 1.1 moles halogenated compound (IV) are reacted.

The solvent employed in the present invention can be from a broad class of polar solvents capable of dissolving or suspending the reactants. Representative solvents include, but are not limited to C-1 to C-10 monohydric alcohols (one OH group), such as methanol, ethanol, n-propanol, iso-propanol, n-butanol, isobutanol, t-butanol, n-pentanol, n-hexanol; dihydric alcohols (two OH groups -diols) such as C-2 to C-10 derivatives including ethylene glycol, propylene glycol, 1,2-butanediol, 1,4-butanediol, pentanediols and the like; or polyhydric alcohols (three OH groups -triols) such as glycerol (1,2,3-propanetriol), 1,2,4-butanetriol, pentaerythritol and the like; alkyl nitriles of the formula R-C≡N wherein R is alkyl of one to ten carbon atoms such as acetonitrile wherein R is methyl; tetrahydrofuran; glycol ethers such ethylene glycol monoethyl ether and propylene glycol monoethyl ether; the chlorinated hydrocarbons such as methylene dichloride, carbon tetrachloride or chloroform; or mixtures of any of the above.

The proton source employed in the present invention can be derived from the reactants themselves, from an optionally added acidic reagent or from any combination thereof. For example the proton source can be derived from the cyanide compound or reactant (III) where hydrogen cyanide is employed or from the α-amino acid reactant (I) in reactions where the salt form of the α-amino acid is employed, such as the hydrochloride (HCl) salt or para-toluenesulfonic acid salt. Other acid salt forms include the formates, acetates or sulfates. Where the proton source is derived from the reactants, either less additional acidic reagent can be employed or no additional acidic reagent may be needed. In situations where the proton source is derived from an optionally added acidic reagent, any suitable mineral or organic acid can be employed. Suitable mineral acids include hydrochloric, sulfuric, sulfonic or phosphoric acids. Suitable organic acids include the C-1 to C-10 alkanoic acids such as formic, acetic, propanoic acids and the like. The additional acidic reagent can be employed in amounts ranging from excess to about 0.5 moles acid: mole α-amino acid (I), more preferably from about 50 to about equimolar, most preferably about equimolar amounts.

The order of addition of the reactants generally is not critical, except that the acyl or acetal compound (II) should be added to the reaction mixture following mixing of the α-amino acid compound (I), cyanide compound (III), Lewis Acid (IV) and solvent, due to the labile nature of the acyl compound (IIa). Preferably, the acyl or acetal (II) is distilled from any solvents, i.e. diethyl phthalate, prior to addition to the reaction mixture. Alternatively, the acyl or acetal compound (II) can be mixed with a suitable solvent as described hereinbefore, before addition to the reaction mixture.

Optionally and preferably, the process is carried out under substantially anhydrous conditions, such those provided by the use of dry reagents and dry reaction vessels. The reactants can also be contacted in the presence of drying agents such as molecular sieves, silica gel, sodium sulfate ($Na_2SO_4$) or magnesium sulfate ($MgSO_4$). In addition, anhydrous conditions can be supplemented by a blanket of an inert gas, such as nitrogen, argon, helium or mixtures thereof.

The present process can be carried out at temperatures effective to give the desired diastereoisomer (X).

The process can be conducted at temperatures ranging from about −100° C. to about 0° C., more preferably from about −60° to about −20° C., most preferably from about −60° C. to about −40° C. The lower temperatures are employed to minimize side reactions of the α-amino acid compound (I), the acyl or acetal compound (II) and the Lewis Acid (IV). Once the acyl or acetal (II) has been added to the reaction mixture, higher temperatures can be employed, such as those ranging from about −60° C. to about 50° C. The process can also be carried out at ambient pressures, with stirring, for a time effective to give the desired completion of the reaction.

Following completion of the reaction, the desired diastereoisomer (X) can be recovered from the reaction mixture by conventional procedures, such as evaporation of any solvents present, filtration, crystallization, chromatography, distillation and the like. Generally, the reaction mixture is filtered to remove any solids i.e. drying agents, diluted with a suitable solvent such as methylene chloride, toluene, diethylether, ethyl acetate and the like, washed with water, treated with a suitable base to adjust the pH to between about 4 to about 7, preferably about 6, to precipitate any tin salts and refiltered. The organic phase containing the diastereoisomer (X) is separated from the aqueous phase and the solvent is removed by distillation or crystallization to give the desired diastereoisomer (X). Alternatively, the diastereomer need not be recovered. For example, the reaction mixture containing the diastereoisomer (X) can contacted with a solvent and acidic reagent such as methanol and hydrochloric acid in order to form the amide (i.e. $—CONH_2$) from the cyano moiety ($—C≡N$).

The desired diastereoisomer (X), thus prepared can be further purified by appropriate stereochemical resolution using conventional procedures, such as crystallization as described in Paul Newman, Optical Resolution Procedures for Chemical Compounds, A publication of the Optical Resolution Information Center, Manhattan College, Riverdale, N.Y. 10471, Volumes 1, 2, 3 and 4 (1984), whose preparative teachings are incorporated herein by reference.

EXAMPLE 1

(S)-N-(1-cyano-2-phenylethyl)-S-phenylalanine hydrochloride

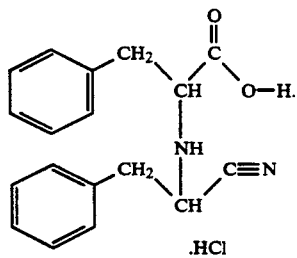

In a four-necked round bottomed flask container, 33.0 g of pulverized molecular sieves (5 Angstom (Å)) and 17.0 g of silica gel are suspended in 167 ml of dry methanol. The mixture is cooled to a temperature of −60° C. and 11.7 ml (0.1 mole) of $SnCl_4$ are added. After the addition of 4.91 g (0.1 moles) NaCN and 20.2 g (0.1 mole) of S-phenylalanine hydrochloride, 20.0 g (0.17 mole) phenacetaldehyde are added dropwise at −60° C.

After one hour of stirring at −60° C. the reaction mixture is allowed to come to room temperature and is stirred for an additional 24 hours. After removal of the molecular sieves and silica gel, the reaction mixture is diluted with 80 ml methylene chloride (CH$_2$Cl$_2$) and 300 ml water. The pH of the reaction mixture is adjusted to 6.0 with about 20 ml of aqueous concentrated ammonia (NH$_3$). The solids are removed and the organic layer is washed with three 60 ml water portions and dried over sodium sulfate. Removal of the solvent gives 22.9 g of the title compound, a yellow oil (yield 77.8%). The compound has a diastereomer ratio of 93% (S,S) and 7% (S,R).

We claim:

1. A process for preparing an (S,S) or (R,R) diastereoisomer of the formula:

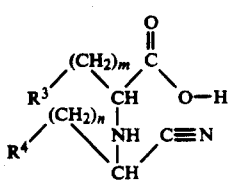  (X)

or salts, esters or amides thereof, wherein R$^3$ and R$^4$ independently represent hydrogen, alkyl, aryl or aryl substituted with halogen, alkyl, nitro or alkoxy, and n and m independently represent integers from one to six, comprising combining a cyanide compound of the formula:

  (III)

wherein M$^1$ is hydrogen, trimethylsilyl or a metal selected from the group consisting of sodium, potassium, lithium, cesium, iron, nickel, cadmium and zinc, with an optionally added proton source, a solvent and a Lewis acid of the formula:

  (IV)

wherein M$^2$ is Sn or Ti and X represents chloro, bromo, fluoro or iodo, with an optically active α-amino acid compound of formula (I):

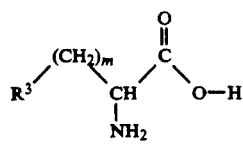  (I)

or salts, esters or amides thereof, wherein R$^3$ and m are as defined hereinbefore, followed by addition of an acyl or acetal compound of formula (II):

  (IIa)

or

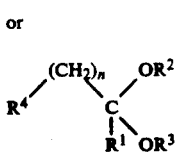  (IIb)

wherein m, n and R$^4$ are as defined hereinbefore, R$^1$ is hydrogen, alkyl or phenyl and R$^2$ and R$^3$ independently represent alkyl.

2. The process of claim 1 wherein the optically active diastereomer (X) is recovered from the reaction mixture.

3. The process of claim 1 wherein diastereoisomer (X), R$^3$ and R$^4$ are hydrogen.

4. The process of claim 1 wherein diastereoisomer (X) is the (S,S) diastereoisomer.

5. The process of claim 1 wherein the cyanide compound (III) is sodium cyanide.

6. The process of claim 1 wherein the solvent is a C-1 to C-10 monohydric alcohol.

7. The process of claim 1 wherein the solvent is methanol.

8. The process of claim 1 wherein a drying agent is employed during the process.

9. The process of claim 1 wherein the process is carried out at a temperature in the range from about −100° to about 0° C.

10. The process of claim 1 wherein the process is carried out at a temperature in the range from about −60° C. to about −20° C.

11. The process of claim 1 wherein the process is carried out at a temperature in the range from about −60° C. to about −40° C.

12. The process of claim 1 wherein the process is carried out using from about 5 moles to about equimolar amounts of acyl or acetal compound (II), from about 10 moles to about equimolar amounts of compound (III), from about 10 moles to about equimolar amounts of compound (IV) and about one mole α-amino acid compound (I).

13. The process of claim 1 wherein the process is carried out by adding a proton source to the reaction mixture.

14. The process of claim 13 wherein the added proton source is a mineral or organic acid.

15. The process of claim 1 wherein the Lewis acid is of the formula M$^2$X$_4$ (IV) wherein M$^2$ and X are as defined hereinbefore.

16. The process of claim 1 wherein the Lewis acid is SnCl$_4$.

* * * * *